United States Patent [19]

Hughes et al.

[11] 4,322,364

[45] Mar. 30, 1982

[54] MODIFIED ISOCYANATE COMPOSITIONS

[75] Inventors: Jeffrey Hughes, Manchester, England; Gerard J. Murray, Dingley, Australia

[73] Assignee: Imperial Chemical Industries Limited, London, England

[21] Appl. No.: 222,143

[22] Filed: Jan. 2, 1981

[30] Foreign Application Priority Data

Jan. 2, 1980 [GB] United Kingdom ............... 00012/80

[51] Int. Cl.³ ................ C07C 119/048; C07C 119/055
[52] U.S. Cl. ...................... 260/453 AM; 260/453 AR; 260/453 AL; 260/453 SP; 521/162; 528/44; 560/35; 560/168; 260/239 A
[58] Field of Search ................ 260/453 AR, 453 AM, 260/453 AL; 560/35, 168

[56] References Cited

U.S. PATENT DOCUMENTS 3,914,269  10/1975  Nersasian ..................... 260/453 PH
4,077,989   3/1978  Schafer et al. ................... 260/404.5

*Primary Examiner*—Dolph H. Torrence
*Attorney, Agent, or Firm*—Cushman, Darby & Cushman

[57] ABSTRACT

A process for the production of a modified isocyanate by reacting a composition containing carbodiimide groups and free isocyanate groups with a diester of an aliphatic dicarboxylic acid in the presence of oxalic or formic acid.

The process permits the production of liquid forms of diphenylmethane diisocyanate useful in the manufacture of polyurethanes.

6 Claims, No Drawings

MODIFIED ISOCYANATE COMPOSITIONS

This invention relates to modified isocyanate compounds and to a process for the production of such modified isocyanate compounds.

In United Kingdom Patent Specification No. 1476088 there is described a process for the conversion of isocyanate in a refined organic isocyanate into carbodiimide groups in the presence of certain types of phosphorus-containing catalysts. The products of the process are useful for the manufacture of polymers such as polyurethanes, and in particular for the manufacture of microcellular elastomers. The process can be used to convert all the isocyanate groups in the isocyanate to carbodiimide groups, but if the product is to be used for the manufacture of polyurethanes, only a proportion (from 3% to 35%) of the isocyanate groups are converted to carbodiimide groups. In these circumstances, the carbodiimide groups react further with the free isocyanate groups to form uretonimine groups according to the following reversible equation:

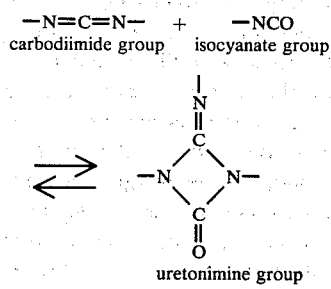

It will be appreciated that for polyisocyanates (i.e. those having two or more isocyanate groups), both the carbodiimide reaction product and the uretonimine reaction product will have unreacted isocyanate groups, and that the effect of the formation of the uretonimine will be to increase the overall isocyanate functionality of the product. Whilst the products obtained by a process such as that described in United Kingdom Patent Specification No. 1476088 are satisfactory for many purposes, it is found that the properties of the polymers formed may generally be improved if the formation of uretonimine groups and the consequent increase in isocyanate functionality is minimized.

United Kingdom Patent Specification No. 1515523 describes a process for the production of modified polyisocyanates in which acylated urea groups are formed by the reaction of carbodiimide-modified polyisocyanates and a carboxylic acid. The compositions provided by the present invention are substantially free from acylated urea groups.

According to the present invention there is provided a process for the production of a modified isocyanate which comprises reacting a composition containing carbodiimide groups and free isocyanate groups with a diester of an aliphatic dicarboxylic acid in the presence of oxalic acid or formic acid.

The diester of the dicarboxylic acid may be a dialkyl, a diaryl or an alkyl aryl ester and the alkyl and aryl radicals may carry substituents. Especially suitable diesters are lower alkyl diesters wherein the aliphatic dicarboxylic acid contains from 2 to 10 carbon atoms and the alkyl radicals may carry substituents such as lower alkoxy and poly(alkyleneoxy) groups. Examples of suitable diesters include dimethyl oxalate, diethyl oxalate, di(2-ethoxyethyl)oxalate, di(monomethoxy polyethylene glycol) oxalate, diethyl malonate, dimethyl succinate, dimethyl glutarate, dimethyl adipate, dimethyl sebacate and mixtures of such diesters. Suitable diaryl esters include diphenyl oxalate. Crude esterification products obtained by reacting oxalic acid with an alcohol often contain both diester and free acid and may be used in the process of the invention without refinement.

The composition containing carbodiimide groups and free isocyanate groups is suitably derived from the conversion of a proportion of the isocyanate groups of an organic isocyanate into carbodiimide groups. The organic isocyanate may be partially converted to the carbodiimide by heating at elevated temperature, but the reaction preferably takes place in the presence of a catalyst. Suitable catalysts are phosphorus-containing catalysts, for example the phosphorus-containing catalysts disclosed in United Kingdom Patent Specification No. 1476088. The reaction is conveniently terminated by deactivation of the catalyst in known manner when the desired proportion of isocyanate groups have been converted to carbodiimide groups and an acid acceptor is optionally incorporated in the reaction mixture.

The dicarboxylic acid diester and the oxalic or formic acid may be added before, during or after the conversion of the isocyanate groups of the organic isocyanate to carbodiimide groups. The diester and acid are suitably added as a mixture and may form the half ester. It will be appreciated that if they are added before or during the conversion to carbodiimide, the composition containing carbodiimide groups and free isocyanate groups may represent a transitory intermediate state, the carbodiimide groups reacting with the diester and acid mixture as they are formed.

The catalyst is optionally deactivated when the desired degree of conversion has been obtained.

If the acid and the diester are added after the conversion of the desired proportion of the isocyanate groups of the organic isocyanate to carbodiimide groups is completed (and to a more limited extent if they are added during the course of the conversion reaction), the composition may contain some uretonimine groups, and indeed if the composition has been allowed to stand for some time after the conversion reaction is completed, all of the carbodiimide groups may have been converted into uretonimine groups. The process of the present invention may equally well be applied to compositions containing uretonimine groups, since the conversion of carbodiimide groups to uretonimine groups is reversible. However, if uretonimine groups are present, it is desirable to heat the composition to a temperature at which the dissociation of uretonimine groups into carbodiimide groups takes place at a sufficiently fast rate. Once again, the composition containing carbodiimide groups and free isocyanate groups may be a transitory intermediate state with the carbodiimide groups reacting with the diester and acid mixture as they are formed from the uretonimine.

The organic isocyanate may be monofunctional or polyfunctional in respect of the isocyanate groups, and may be a refined organic isocyanate or a crude organic isocyanate.

By the term "refined" we mean an isocyanate which has been subjected to a purification process such as distillation or crystallization or a combination of such processes. In contrast a "crude" organic isocyanate will not have been subjected to such purification processes and may contain polymeric material or material of a range of different isocyanate polyfunctionality.

Examples of suitable organic isocyanates include phenyl isocyanate, tolyl isocyanates, chlorophenyl isocyanates, naphthyl isocyanates, tolylene-2,4 and 2,6-diisocyanates and mixtures thereof, p-phenylene diisocyanate, chlorophenylene diisocyanates, hexamethylene diisocyanate and 4,4'-diphenylmethane diisocyanate and mixtures of this isomer with other isomers thereof or, in the product known as "crude MDI", with methylene bridged polyphenyl polyisocyanates of higher functionality.

The invention is particularly useful when applied to aromatic polyisocyanates i.e. those having two or more isocyanate groups. Examples of such isocyanates include tolylene diisocyanates especially the well-known commercially available mixtures of the 2,4- and 2,6-isomers thereof and diphenylmethane diisocyanates. Mixtures of polyisocyanates may also be used.

Refined, i.e. distilled or crystallized 2,4'- and 4,4'-diphenylmethane diisocyanates are solids melting at about 36° C. and 40° C. and the invention is particularly applicable to such isocyanates or mixtures of these, since the process of the invention gives liquefied compositions which are particularly useful in polyurethane formulations in that they can be incorporated at room temperature without the difficulties inherent at their incorporation as solids or above the melting point. Furthermore the process of the invention minimizes the increase of isocyanate functionality associated with the formation of uretonimine groups, and in general leads to polyurethane elastomers of improved tensile and elongation properties as compared with polyurethane elastomers derived from isocyanate compositions containing uretonimine groups.

The process of the present invention is also applicable to crude mixtures such as the commercially available product known as crude MDI. Crude MDI is a mixture of methylene bridged polyphenyl polyisocyanates generally containing from 30% to 85% by weight of diphenylmethane diisocyanate, the remainder being methylene bridged polyphenyl polyisocyanates of higher functionality together with the by-products formed in the manufacture of such polyisocyanates by phosgenation. Crude MDI is liquid at ambient temperatures, but nevertheless tends to be unstable with respect to separation of crystals of 4,4'-diphenylmethane diisocyanate under winter storage or transport conditions. The process of the present invention seeks to provide liquid compositions which are stable to storage and do not form a sediment on standing, and in which the increase of isocyanate functionality and viscosity associated with the formation of uretonimine groups is minimized.

As noted previously, the dicarboxylic acid diester and the oxalic or formic acid may be added before, during or after the conversion of the isocyanate groups of the organic isocyanate to carbodiimide groups. Thus they may be added for example with the catalyst at the start of the carbodiimide formation reaction or at any time during the course of the carbodiimide formation reaction. Conventional reaction conditions, for example a temperature of 80° to 150° C., or more preferably 90° to 130° C., may be used. If the diester and acid are added to an isocyanate which has already been modified by the conversion of a proportion of the isocyanate groups to carbodiimide groups, the composition is preferably heated to facilitate reaction of the diester of oxalic acid with the carbodiimide groups and to convert any uretonimine groups which may be present to carbodiimide groups. The composition is suitably heated at a temperature of from 80° to 220° C. and more preferably at a temperature of from 130° to 200° C. In general, oxalic acid is preferred to formic acid because it permits the use of milder reaction conditions.

The proportion of the diester of the dicarboxylic acid used is suitably from 0.1 to 2.0 moles per gram equivalent of carbodiimide functionality. The oxalic or formic acid is conveniently used in an amount of from 0.3 to 1.5 gram equivalents per mole of the diester. Preferably, the diester is used in an amount of from 0.2 to 1.5 moles per gram equivalent of carbodiimide functionality and the oxalic or formic acid is used in an amount of from 0.8 to 1.2 gram equivalents per mole of diester. A mixture of oxalic and formic acids may be used. It will not in general be possible to measure directly the total carbodiimide content of a given composition to be reacted with the diester if for example the acid and diester are added before or during the carbodiimide formation reaction, or if the composition contains uretonimine groups. However the total carbodiimide content which is to be reacted with the diester of oxalic acid may be readily determined from the proportion of the isocyanate groups which have been (or which are to be) converted to carbodiimide/uretonimine groups. Thus if for example it is desired to convert 30% of the isocyanate groups of a diphenylmethane diisocyanate to carbodiimide, this would result in the formation of 0.15 equivalents of carbodiimide functionality per mole of diphenylmethane diisocyanate and would require from 0.015 to 0.3 moles of diester of oxalic acid per mole of diphenylmethane diisocyanate.

In the carbodiimide formation reaction, the product is obtained by deactivating the catalyst when the desired proportional conversion of isocyanate groups has been achieved. The desired proportional conversion of isocyanate groups is thus decided in advance and it is a simple matter to add the appropriate proportion of acid and diester before or during the reaction.

It is a particular advantage of the process of the present invention that the modified isocyanate composition formed is relatively stable with respect to the formation, over a period of time, of uretonimine groups. In general the formation of uretonimine groups is not significant within the normal storage life of the composition.

Whilst the Applicants do not wish to be bound by any particular theory, it is believed that the use of a diester of the formula:

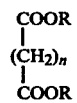

wherein R is an optionally substituted alkyl or aryl radical and n is zero or a whole number, in the process of the invention, gives modified isocyanates containing structural units of the formula:

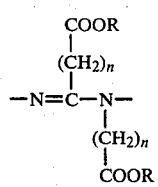

The presence of such units has been demonstrated by nuclear magnetic resonance, mass spectrometer and infra-red examination.

The modified isocyanates made by the process of the invention, especially those made from aromatic polyisocyanates such as diphenylmethane diisocyanate, are useful in the manufacture of polyurethanes, particularly elastomers and flexible foams, including microcellular elastomers, using conventional preparative methods.

The invention is illustrated by the following Examples in which all parts and proportions are by weight unless otherwise stated.

EXAMPLE 1

250 Parts of pure 4,4'-diphenylmethane diisocyanate were heated to 50° C. with stirring under dry nitrogen. 0.1 Parts of dimethylamino ethanol was added and the temperature raised to 105° C. over 15 minutes. 0.00125 Parts of 1 phenyl-3-methyl phospholene oxide was then added and the mixture stirred at 105° C. until the isocyanate value was 30%. 16 Parts of a mixture of diethyl oxalate and oxalic acid, in the ratio 5:1 by weight, were added along with 0.0375 part of thionyl chloride. The temperature was maintained at 105° C. throughout the addition and for 30 minutes after. The product (A) a pale yellow liquid of viscosity 70 cp at 25° C., was cooled quickly to 25° C. and the final NCO value was 26.5%.

Infra-red analysis showed there to be no absorption at 1360 cm$^{-1}$.

The product remained liquid even on prolonged storage at 0° C.

A similar experiment to the above was carried out without the diethyl oxalate oxalic acid mixture. A product (B) having a substantial uretonimine band at 1360 cm$^{-1}$ was formed.

Example 1 was repeated replacing oxalic acid by an equivalent amount of
(a) salicylic acid
(b) malonic acid
(c) dimethyl malonic acid
(d) adipic acid
(e) succinic acid.

In each case the final product exhibited strong absorption in the infra red at 1360 cm$^{-1}$ indicating the presence of substantial quantities of uretonimine.

EXAMPLE 2

250 g of pure 4,4'-diphenylmethane diisocyanate were heated to 50° C. with stirring under dry nitrogen. 0.76 ml 10% wt/vol solution of epichlorohydrin in perchloroethylene was added and the temperature raised to 115° C. 0.00125 g of 1-phenyl-3-methyl phospholene-1-oxide was added and the mixture stirred until the isocyanate value was 30%. 7 g of diethyl oxalate, 4 g of oxalic acid and 0.0125 g of thionyl chloride were added maintaining the temperature at 115° C. for 30 minutes after the addition. The product was cooled to 25° C. and the final NCO value was 26.7%.

Infra red analysis indicated the absence of uretonimine groups. No uretonimine was observed even after standing at ambient temperature for several months. On storage at 0° C. for several weeks the material remained a mobile liquid with no apparent crystallization of 4,4'-diphenylmethane diisocyanate occurring.

EXAMPLE 3

Example 2 was repeated replacing the oxalic acid by 2 g and then 4 g of formic acid.

In the former case, infra red analysis showed the presence of a trace of uretonimine but the increased amount of formic acid gave no detectable amount of uretonimine.

EXAMPLE 4

Example 2 was repeated replacing the diethyl oxalate by 24.8 g of diethyl sebacate. The product had an isocyanate value of 26.5% and no detectable amount of uretonimine.

EXAMPLE 5

Example 2 was repeated replacing the diethyl oxalate by 14 g of ethyl phenyl oxalate. The product was a pale yellow liquid with no detectable amount of uretonimine.

EXAMPLE 6

Example 2 was repeated using 7.7 g of diethyl malonate instead of the diethyl oxalate. The product was a hazy yellow liquid with no detectable amount of uretonimine.

EXAMPLE 7

Example 1 was repeated using a mixture of 14.6 g of dimethyl succinate and 2.75 g of oxalic acid instead of the 5/1 wt/wt mixture of diethyl oxalate/oxalic acid. A cloudy yellow liquid product was obtained with no detectable amount of uretonimine.

EXAMPLE 8

Example 1 was repeated using a mixture of 11.3 g of di-(2-ethoxyethyl)oxalate and 4.0 g of oxalic acid in place of the 5/1 wt/wt mixture of diethyl oxalate/oxalic acid mixture. A pale yellow liquid of NCO value 23.4% was obtained which contained no detectable amount of uretonimine.

EXAMPLE 9

Example 2 was repeated using 12 g of diphenyl oxalate in place of the diethyl oxalate. A yellow liquid was obtained which contained no detectable amount of uretonimine.

EXAMPLE 10

Example 2 was repeated using 10.6 g of diethyl phthalate instead of diethyl oxalate. A viscous liquid containing substantial quantities of uretonimine was obtained.

EXAMPLE 11

Example 2 was repeated using 7.4 g of ethyl formate instead of diethyl oxalate. A viscous liquid containing quantities of uretonimine was obtained.

EXAMPLE 12

5000 g of pure 4,4'-diphenylmethane diisocyanate were heated to 50° C. with stirring under a blanket of dry nitrogen. 1.5 ml of a 10% wt/vol solution of epichlorohydrin in perchloroethylene were added and the temperature raised to 115° C. 0.025 g of 1-phenyl-3-methyl phospholene oxide was added and the mixture stirred until the isocyanate value was 27%. 140 g of diethyl oxalate, 80 g of oxalic acid and 0.25 ml of thionyl chloride were added and the temperature was maintained at 115° C. for 0.5 hour after this addition. The product was cooled to ambient temperature and the resultant pale yellow liquid had an isocyanate value of 23.8% and a viscosity of 200 cp at 25° C. The product remained liquid even on storage at 0° to −5° C. for several months. Again no uretonimine groups were detected on infra-red analysis.

EXAMPLE 13

250 g of a diphenylmethane diisocyanate isomer mixture containing 80% 4,4′-, 19% 2,4′- and 1% 2,2′-isomers were heated to 50° C. with stirring under a blanket of dry nitrogen. 0.76 ml of epichlorohydrin was added and the temperature raised to 115° C. when 1.25 ml of a 0.1% wt/vol 1-phenyl-3-methyl phospholene-1-oxide solution in perchloroethylene were added. The mixture was stirred at 115° C. until the isocyanate value was 29% when 13.3 g of diethyl oxalate and 2.7 g of oxalic acid were added as a homogeneous solution, followed by 0.0125 g of thionyl chloride. The temperature was maintained at 115° C. for 0.5 hr and the product cooled to ambient temperature. The yellow product had an isocyanate value of 24.7% and exhibited no detectable absorption in the infra-red due to uretonimine groups.

EXAMPLE 14

1925 g of a diphenylmethane diisocyanate isomer mixture containing 94% 2,4′-, 3.5% 2,2′- and 2.5% 4,4′-isomers were heated to 50° C. with stirring under a blanket of dry nitrogen. 3.2 ml of epichlorohydrin were added and the temperature was raised to 115° C. when 1 ml of a 1% wt/vol solution of 1-phenyl-3-methyl phospholene-1-oxide in perchloroethylene was added. The mixture was stirred at 115° C. until the isocyanate value was 28.5% when 56 g of diethyl oxalate and 32 g of oxalic acid were added as a homogeneous solution followed by 0.1 ml of thionyl chloride. The mixture was heated for a further 1.25 hours at 105° C. and then cooled to ambient temperature. The yellow liquid product had an isocyanate value of 24.1% with no detectable uretonimine groups. The isocyanate value was adjusted to 24.7% by addition of an appropriate amount of the starting isocyanate composition.

EXAMPLE 15

Flexible foam mouldings were prepared in the laboratory, using the procedure known in the art, from the modified isocyanates of Examples 13 and 14, i.e. isocyanate compositions C and D respectively, and the following formulations.

|  | Parts by Weight | |
|---|---|---|
|  | Foam I | Foam II |
| Oxypropylated glycerol with 16.5% ethylene oxide as a tip, mol. wt. 6000 | 100 | 100 |
| Water | 3.0 | 3.0 |
| Dabco 33LV (Air Products) | 1.0 | 1.0 |
| Catalyst A1 (Union Carbide) | 0.1 | 0.1 |
| Silicone B4113 (Goldschimdt) | 1.0 | 1.0 |
| Refrigerant 11 | 10 | 10 |
| Isocyanate C | 57.2 | — |
| Isocyanate D | — | 57.2 |

The foams had the following physical properties:

|  | Foam I | Foam II |
|---|---|---|
| Density (Cut) kgm$^3$ | 35 | 34 |
| Compression Hardness kNm$^{-2}$ at 65% compression | 5 | 8.3 |

EXAMPLE 16

Reaction Injection Moulded test sheets were prepared using the method known in the art from the isocyanate product of Example 2 and the following formulation.

A resin blend was prepared as follows:

|  | Parts by weight |
|---|---|
| Polypropylene glycol with 20% ethylene oxide tip. Hydroxyl value 29 mg KOH/g | 80 |
| Oxypropylated glycerol with 20% ethylene oxide tip. Hydroxyl value 29 mg KOH/g | 20 |
| Ethylene glycol | 15.2 |
| Triethylene diamine | 0.5 |
| Dibutyl tin dilaurate | 0.05 |
| Water content was adjusted to 0.15% | |

The above blend was mixed in the wt. ratio 100 blend/80 isocyanate product and test sheets were moulded. The averaged physical properties were as follows:

| Density kgm$^{-3}$ | 1000 |
|---|---|
| Hardness Shore D | 51 |
| Tensile Strength kNm$^{-2}$ | 16,500 |
| Elongation at Break % | 220 |
| Tear Strength (angle) Nm$^{-1}$ | 61,500 |
| Flexural modulus at ambient MNm$^{-2}$ | 150 |
| −30° C. | 470 |
| −70° C. | 69 |

EXAMPLE 17

Mouldings of microcellular elastomers were prepared, using the method known in the art, from the isocyanate product of Example 1 and the following formulation:

A resin blend was prepared as follows:

|  | Parts by weight |
|---|---|
| Polypropylene glycol with 20% ethylene oxide tip, mol. wt. 3750 | 68.24 |
| Oxypropylated glycerol with 15% ethylene oxide tip, mol. wt. 5250 | 17.06 |
| 1,4-Butane diol | 8.6 |
| Ethylene glycol | 0.29 |
| Triethylene diamine | 0.4 |
| Dibutyl tin dilaurate | 0.02 |
| Refrigerant 11 | 5.5 |
| Water adjusted to | 0.18% |

This blend was intimately mixed with the products of Example 1 in the ratios:

Product A: 43.0/100 resin blend, isocyanate index 100

Product B: 35.8/100 resin blend, isocyanate blend 100.

Individual mouldings were prepared by pouring the isocyanate/resin mixture into a flat rectangular mould.

Physical properties of the resulting elastomers were as follows:

|  | Product A | Product B |
| --- | --- | --- |
| Density, kg.m$^{-3}$ | 540 | 540 |
| Hardness, Shore A | 71 | 72 |
| Tensile Strength, kN.m$^{-2}$ | 3220 | 2950 |
| Elongation at break, % | 230 | 180 |

The higher tensile strength and elongation of Product A demonstrate the superiority of the modified isocyanate over the unmodified material.

EXAMPLE 18

Example 2 was repeated except that the diethyl oxalate/oxalic acid mixture was added to the isocyanate at the same time as the phospholene oxide. After reacting for 2¾ hours at 115° C., a liquid product of isocyanate value 26.3% was obtained which was free from uretonimine.

We claim:

1. A process for the production of a modified isocyanate which comprises reacting a composition containing carbodiimide groups and free isocyanate groups with from 0.1 to 2.0 moles per gram equivalent of carbodiimide functionality of a diester of an aliphatic dicarboxylic acid and from 0.3 to 1.5 gram equivalents of oxalic or formic acid per mole of diester.

2. A process according to claim 1 wherein the diester has the formula

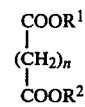

wherein each of $R^1$ and $R^2$, independently, is lower alkyl, lower alkoxy lower alkyl or phenyl and n is an integer from 0 to 8.

3. A process according to claim 2 wherein the diester is a diester of oxalic acid.

4. A process according to claim 1 wherein the composition containing carbodiimide groups and free isocyanate groups is a composition obtained by converting a proportion of the isocyanate groups in diphenylmethane diisocyanate to carbodiimide groups.

5. A process according to claim 1 wherein the diester is used in an amount of from 0.2 to 1.5 moles per gram equivalent of carbodiimide functionality.

6. A process according to claim 1 wherein the oxalic or formic acid is used in an amount of from 0.8 to 1.2 gram equivalents per mole of diester.

* * * * *